United States Patent [19]

Gjelsnes et al.

[11] Patent Number: 5,739,902
[45] Date of Patent: Apr. 14, 1998

[54] LIQUID FLOW CYTOMETER

[76] Inventors: Oddbjørn Gjelsnes, Gladvollterrasse 2., 1168 Oslo; Reidar Tangen, Herregårdsveien 57B, N-1168, Oslo, both of Norway

[21] Appl. No.: 553,627
[22] PCT Filed: Jun. 8, 1994
[86] PCT No.: PCT/NO94/00106
    § 371 Date: Jan. 23, 1996
    § 102(e) Date: Jan. 23, 1996
[87] PCT Pub. No.: WO94/29695
    PCT Pub. Date: Dec. 22, 1994

[30] Foreign Application Priority Data

Jun. 8, 1993 [NO] Norway ............... 932088

[51] Int. Cl.⁶ .................. G01N 15/02; G01N 21/00; G01J 4/00
[52] U.S. Cl. .................. 356/73; 356/336; 356/338; 356/343; 356/341; 356/364
[58] Field of Search ............... 356/39, 72, 73, 356/336, 318, 343, 335–339, 364, 417, 246, 301, 317, 341; 250/283, 461, 458.1, 459.1, 461.1, 461.2, 573–575; 350/394, 293, 296, 283; 209/552, 606, 643, 576, 577, 579, 644

[56] References Cited

U.S. PATENT DOCUMENTS

| | | | |
|---|---|---|---|
| 4,281,924 | 8/1981 | Auer et al. | 356/73 |
| 4,662,742 | 5/1987 | Chupp | 356/39 |
| 5,030,002 | 7/1991 | North, Jr. | 356/73 |
| 5,040,890 | 8/1991 | North, Jr. | 356/72 |
| 5,179,026 | 1/1993 | Matsuda et al. | 436/17 |

FOREIGN PATENT DOCUMENTS

| | | |
|---|---|---|
| 0442025 | 8/1991 | European Pat. Off. . |
| 0538551 | 4/1993 | European Pat. Off. . |
| 0539743 | 5/1993 | European Pat. Off. . |
| P91427 | 5/1993 | Norway . |
| 2238612 | 6/1991 | United Kingdom . |

OTHER PUBLICATIONS

International Pub. No. WO 93/07471 to W. Kaye entitled, "Detecting A Radiation Signal," dated 15 Apr. 1993.

*Primary Examiner*—Frank G. Font
*Assistant Examiner*—Michael P. Stafira
*Attorney, Agent, or Firm*—Watson Cole Stevens Davis, P.L.L.C.

[57] ABSTRACT

A liquid flow cytometer for counting and classification of particles such as biological cells and other microscopic particles in liquids that involves an optical system for irradiation and detection in a metering zone (7), thus enabling optical dispersion and fluorescence caused by the particles to be simultaneously detected when the particles pass the metering zone, includes in a first beam path ($S_1$) a mirror reflector (9) with its focal point in the metering zone (7), a quarter-wave plate (8) between the metering zone (7) and the mirror reflector (9), a lens (6) with its focal point in the metering zone (7) and located on the opposite side of it together with a dichroic mirror (5) behind the lens and provided in such a manner that it gives reflection to a second beam path ($S_2$). In the second beam path ($S_2$) a beam splitter (4) is provided between the dichroic mirror (9) and a known per se light source (1), and produces a third beam path ($S_3$). The cytometer includes a first detector (13) provided in the first beam path ($S_1$) behind the dichroic mirror (5) and arranged for the detection of fluorescence emitted by the particles in the metering zone (7), together with a second detector (16) provided in the third beam path ($S_3$) and arranged for the detection of optical dispersion caused by the particles in the metering zone (7).

11 Claims, 4 Drawing Sheets

LIQUID FLOW CYTOMETER

BACKGROUND OF THE INVENTION

1. Field of the Invention

The invention concerns a liquid flow cytometer for counting and classification of particles such as biological cells or other microscopic particles in liquids, where the cytometer includes an optical system for irradiation and detection in a metering zone, thus enabling optical dispersion and fluorescence caused by the particles to be simultaneously detected when the particles pass the metering zone.

2. The Prior Art

The use of cytometers based on optical dispersion is known in the prior art for counting and classification of microscopic particles in a liquid. This prior art is illustrated schematically in FIGS. 1–3, where FIG. 1 shows the flow system with a flow cell, FIG. 2 shows a hydrodynamic focusing device assigned to the flow cell, and FIG. 3 shows the detector device for optical dispersion caused by particles in the flow cell. In FIG. 1 the sample is fed into a flow cell together with a transport liquid in the form of filtered water which is pumped into the flow cell from a container. The transport liquid and the sample, i.e., those particles which have to be counted and classified pass through the flow cell, a pump system and a filter which removes particles, after which the transport liquid, i.e., filtered water, is passed back to the container. In the flow cell there is provided a hydrodynamic focusing device in flow connection with the actual flow cell which is composed of a capillary tube. The hydrodynamic focusing device is in the form of a conical nozzle which tapers towards and leads into the capillary tube. The sample is passed into the nozzle through a thin tube in the centre of the nozzle and is carried along with the transport water in such a manner that the sample is accelerated towards the mouth of the nozzle and the capillary tube. By directing a focused beam of preferably monochromatic, coherent light onto the flow cell, the particles in the liquid will cause a scattering or dispersion of the light. The scattered light is focused by a lens device on to a photodetector and the intensity of the detected, scattered light will be a measure of the degree of dispersion which in turn is related to the number of particles in the metering zone and their size. In order to prevent the light from the laser beam from entering the detector there is positioned between the flow cell and the focusing device a beam stop which forms a shield against the direct radiation from the laser, but which substantially does not impair the scattered light.

A cytometer which is substantially based on the above-mentioned principles and is suitable for detection, counting and classification of biological cells and other microscopic particles in liquids is known from Norwegian patent application No. 91 427, which hereby is incorporated as reference.

There are also known cytometers and similar instruments for the detection of particles based on the use of fluorescence which is emitted by the particles when they are irradiated with light from a light source. One example of a detector of this kind is known from EP-A1-0539 743, in which there is disclosed a collimator in the form of a parabolic reflector 40 which permits a more efficient use of bandpass filters in order to block scattered radiation during detection.

U.S. Pat. No. 4,662,742 discloses a flow cytometry apparatus including an optical path with a beam splitter to transmit fluorescence and reflect scatter. EP-A-0538551 discloses a flow cytometer for the detection of fluorescence above.

The need for stable, reliable and sensitive analytical instruments for the determination of microbial and cellular content in liquids such as water, beverages, oils and bodily fluids is constantly increasing.

By means of liquid flow cytometry biological particles which are in suspension can be counted and classified in a rapid and reliable manner. As mentioned above, according to this method the particle sample is fed along with a transport liquid and care is normally taken to ensure that the particles pass substantially one at a time through the flow cell where they are subjected to the impact of an intense beam of light, the result of which is that the particles can be counted individually and measured with regard to light scatter and fluorescence. At present, liquid flow cytometry is routinely employed principally for the analysis of white blood cells (leukocytes), and in the field of bacteriology liquid flow cytometry has only been used for research purposes.

Cells such as leukocytes are very large in proportion to microbes such as, e.g., enterobacteria. Consequently the requirement for stability and sensitivity for a liquid flow cytometer which is to be routinely employed in the field of microbiology is therefore much greater than for a cytometer for use in haematology.

Thus a first object of the present invention is to provide a liquid flow cytometer which is sufficiently stable and sensitive to enable it to be generally employed in the field of microbiology, but which can naturally also be used in the known manner for counting and classification of blood cells in mammals.

A second object of the present invention is to provide a liquid flow cytometer which provides an improved irradiation of the particles and a better collection both of scatter light and fluorescent light caused by the particles, thus enabling the sensitivity to be increased.

A further object of the present invention is to provide a liquid flow cytometer which can be used simultaneously for the detection of both optical dispersion and fluorescence, without the need for a complicated optical system for this purpose.

Yet another object of the present invention is therefore to simplify the optical system and to integrate detectors and optical system, thus providing a liquid flow cytometer with fewer optical components and reduced physical dimensions, which in turn will help to improve the instrument's stability and also lead to lower production costs.

SUMMARY OF THE INVENTION

The above-mentioned and other objects are achieved according to the present invention with a liquid flow cytometer which is characterized in that the optical system in a first beam path comprises a mirror reflector with its focal point in the metering zone, a quarter-wave plate between the metering zone and the mirror reflector, a lens with its focal point in the metering zone and located on the opposite side of it, together with a dichroic mirror behind the lens and arranged in such a manner that it gives a partial reflection substantially orthogonally to the axis of the lens, the reflection direction being in a second beam path of the optical system, and in the second beam path a beam splitter located between the dichroic mirror and an as per se known light source, the beam splitter producing a third beam path substantially orthogonally to the second beam path, that the cytometer further comprises a first detector provided in the first beam path behind the dichroic mirror and arranged for the detection of fluorescence emitted by the particles in the metering zone, together with a second detector provided in the third beam path and arranged for the detection of optical dispersion caused by the particles in the metering zone.

BRIEF DESCRIPTION OF THE DRAWINGS

The fluid flow cytometer according to the present invention will now be described in more detail in connection with an embodiment and with reference to the attached drawings, wherein FIGS. 1, 2 and 3 as mentioned above illustrate the prior art, while FIG. 4 schematically illustrates an optical system for a fluid flow cytometer according to the present invention.

DETAILED DESCRIPTION OF THE PREFERRED EMBODIMENT

Figure 4:
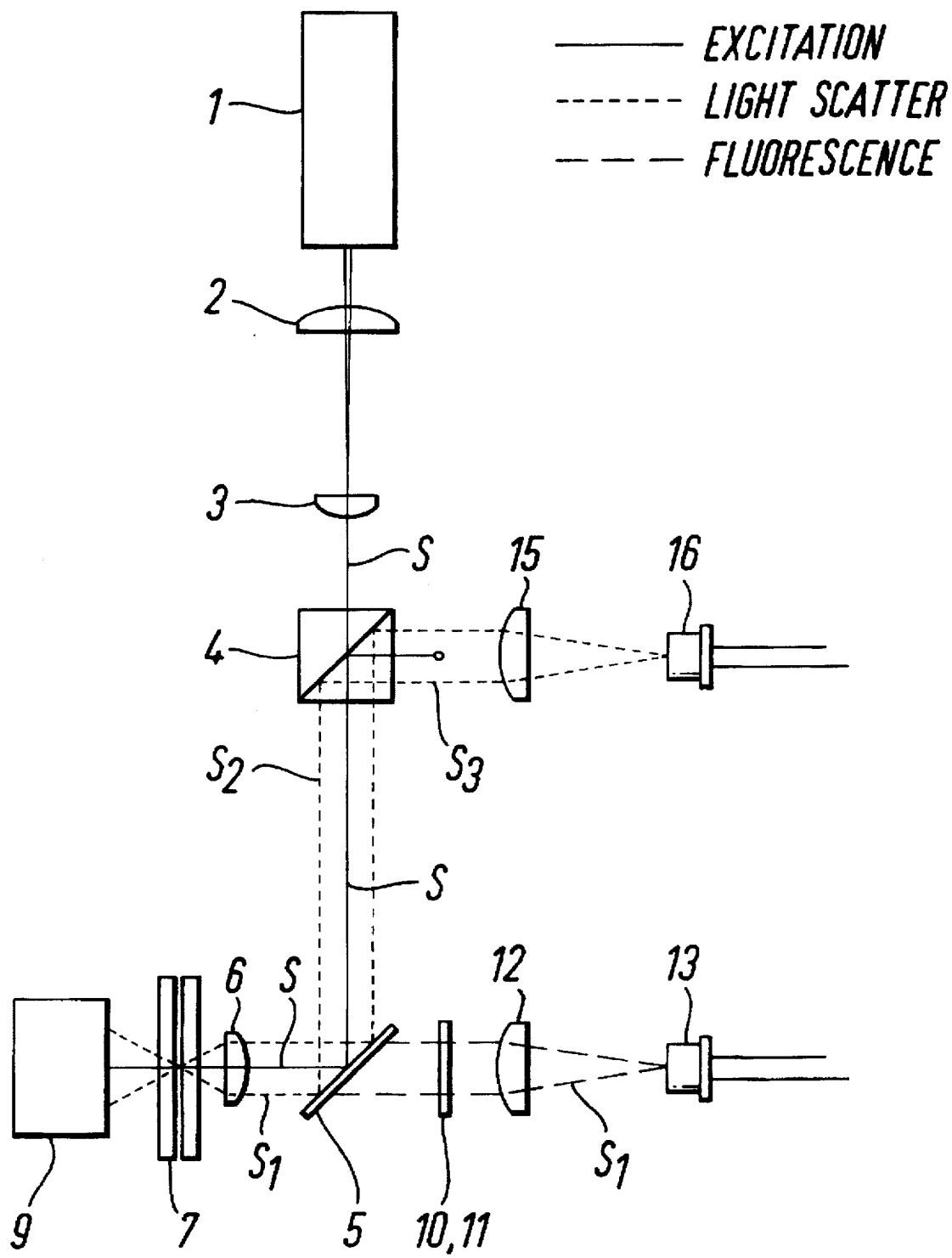

The optical system of a fluid flow cytometer according to the present invention is illustrated in FIG. 4. Light from a laser 1 is focused and collimated to a beam S which passes through a beam splitter 4 in a beam path $S_2$ and is reflected by a dichroic filter or mirror 5 through the metering zone or flow cell 7 which here is in the form of a capillary tube and into an excitation amplifier. The capillary tube 7 and excitation amplifier 9 are located in an additional beam path $S_2$. The laser beam S passes through the flow cell 7 and returns from the excitation amplifier 9, since it is focused on the flow cell 7 by the excitation amplifier 9, and a lens 6 provided between the dichroic mirror and the flow cell respectively. Thus the laser beam passes twice through the flow cell and any particles in this will now cause a light scatter and possibly also fluoresce. The fluorescent light passes through the dichroic mirror and continues in the beam path $S_1$ to a fluorescence detector, while the scattered light is reflected back to the beam path $S_2$ and on to the beam splitter where it is exposed to a further reflection of yet another beam path $S_3$ and ends in a detector for light scatter.

With this embodiment the object is achieved that two different detection principles can be employed in one and the same optical system, while at the same time an intensification is achieved of the light which is used for the two detection mechanisms.

Figure 1:
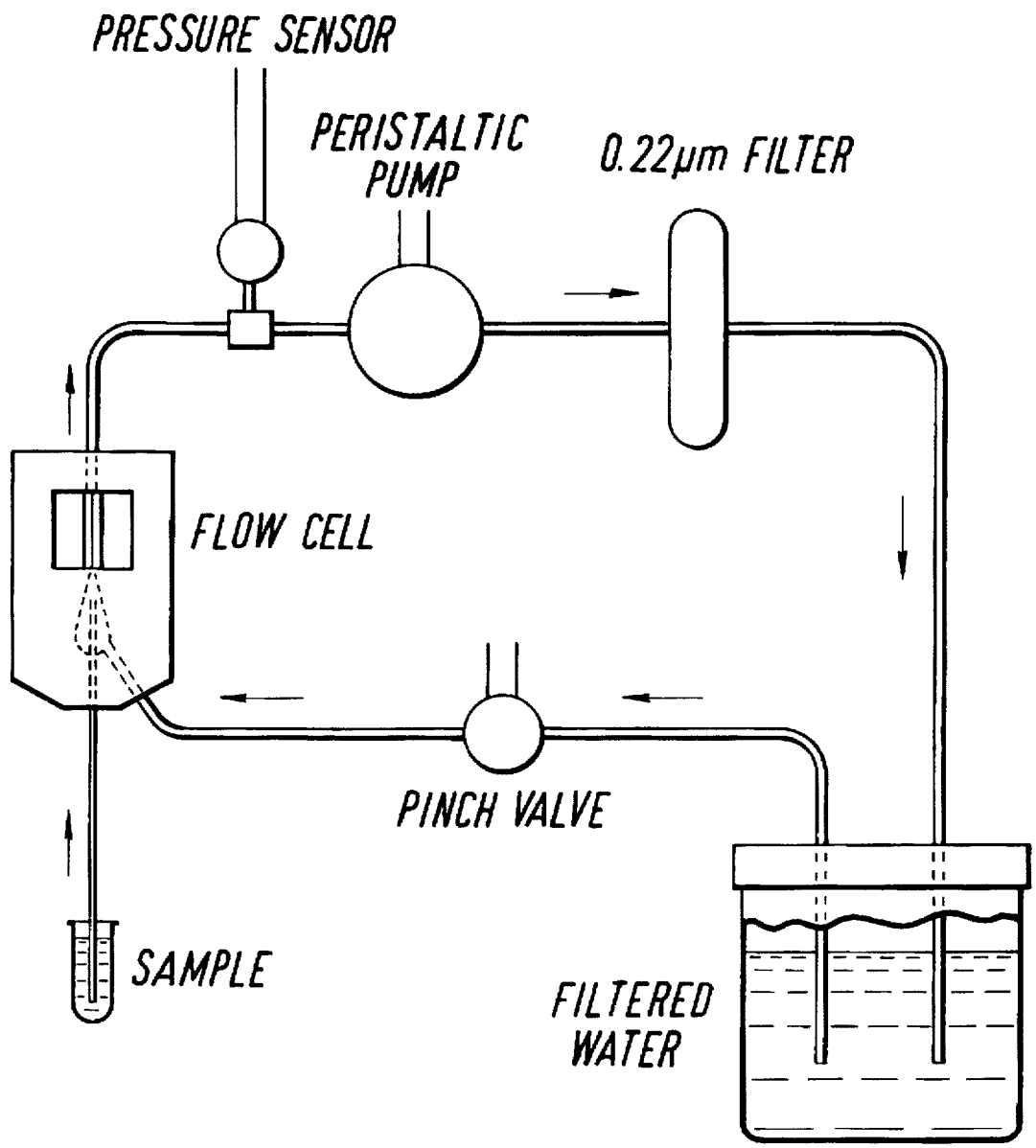
Figure 2:
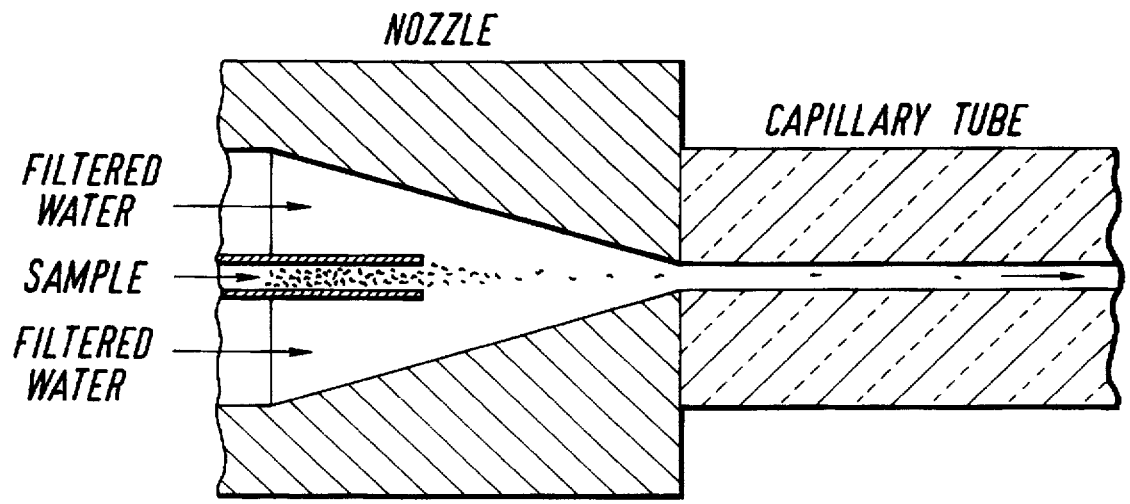
Figure 3:
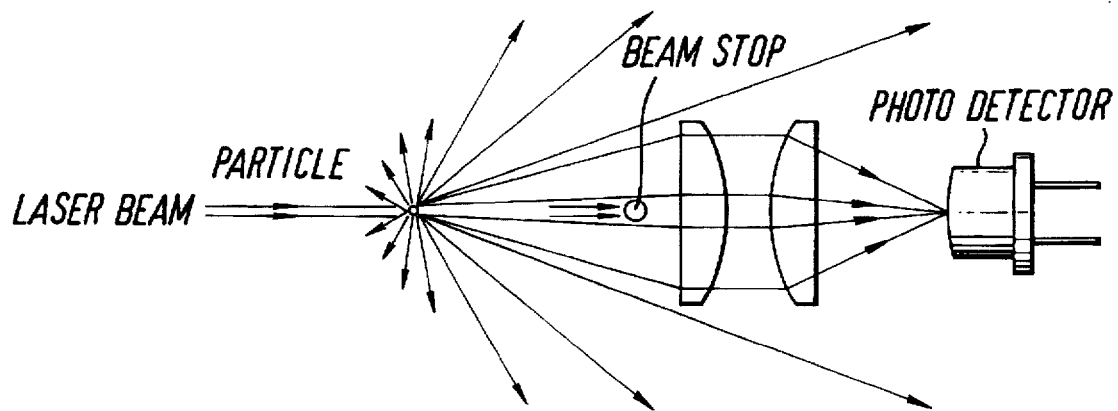
Figure 5:
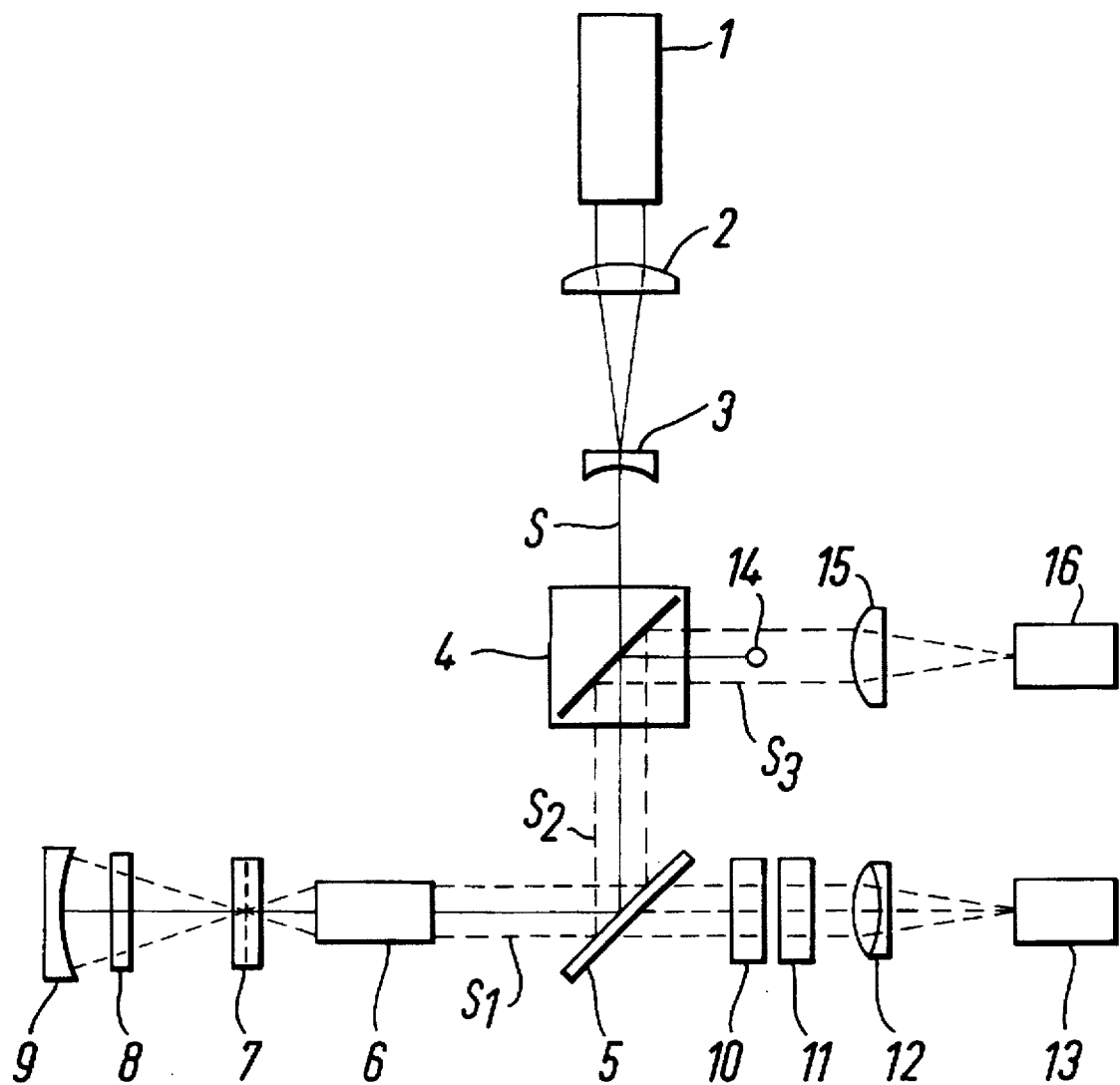
FIG. 5 shows in rather more detail those components which form part of the fluid flow cytometer in FIG. 4.

The liquid flow cytometer according to the present invention is illustrated in some more detail in FIG. 5 where the three beam paths are indicated in the same way as in FIG. 2. A light source 1, preferably a diode laser, emits a monochromatic, coherent beam S of polarized light of polarized light and this beam S is focused and collimated by a lens device 2,3, which comprises a planoconvex lens 2 and planoconcave lens 3. The beam S passes through a polarizing beam splitter 4 which can be designed as a cubiform body and strikes a dichroic mirror or filter 5 which produces a beam path $S_1$, substantially orthogonally to the beam path $S_2$. The laser beam S reflected by the dichroic filter 5 is focused on the metering zone or flow cell 7 by a lens 6 which can be an ordinary microscope objective and thereafter passes a quarter-wave plate 8 located in the beam path $S_1$, which plate causes a polarizing rotation of the laser light by $\pi/4$. The light then strikes an excitation amplifier in the form of the mirror reflector 9 which like the lens 6 has its focal point in the metering zone 7, the mirror reflector 9 which can preferably be a spherical concave mirror, once again reflecting the light through the quarter-wave plate 8, where it once more receives a polarizing rotation of $\pi/4$ and passes through the metering zone 7. The light from the laser 1 has thereby passed twice through the metering zone 7 and each time is scattered by the particles in the metering zone or causes these to emit fluorescent light. Both the scattered light and the fluorescent light pass through the lens 6 and strike the dichroic mirror 5. The scattered light which is rotated by 90° in relation to the laser beam's polarization angle, is reflected by the dichroic mirror 5 and passed back along the beam path $S_2$ to the beam splitter 4 where due to the altered polarization plane it is reflected to a further beam path $S_3$. In the beam path $S_3$ there is provided a beam stop 14 which causes the narrow, collimated laser beam to be blocked, while the scattered light passes substantially unimpaired to a lens device 15, e.g. in the form of a planoconvex lens with a long focal length, which focuses the scattered light on a detector 16 for detection of the optical dispersion. A photodiode, for example a PIN diode, is preferably used as the detector 16.

If those particles which have to be detected are fluorescent, they will as mentioned also emit fluorescent light. If particles are not intrinsically fluorescent, they can be tagged with one or more fluorochromes which have an absorption corresponding to the wavelength of the light source and in both cases the particles will fluoresce when they pass through the metering zone 7 and are irradiated by the laser beam. The fluorescent light is intercepted directly by the lens 6 and indirectly via the mirror reflector 9. The fluorescent light will have a longer wavelength than the excitation light, i.e. the laser beam, and passes unreflected through the dichroic mirror 5 and continues on the beam path $S_1$ to a fluorescence detector 13 which preferably employs a photodiode and particularly a silicon avalanche diode. In order to eliminate any remains of scattered light which have passed through the dichroic mirror 5 and continued on the beam path $S_1$, there are provided optical filters 10,11 in the beam path $S_1$, between the dichroic mirror 5 and a lens device 12 which focuses the fluorescent light on the detector 13. The optical filters 10,11 have a passband which lets through the fluorescent light which has a longer wavelength than the laser light. The lens device 12 for focusing can preferably be an achromatic lens with a long focal length.

Since both the scattered light and the fluorescence from the particles which have to be detected are directly intercepted via the lens 6 and indirectly via the mirror reflector 9, thereby passing the metering zone 7 twice, the effective light collection is increased as well as the intensity of both the light dispersion and the fluorescence. It should be noted that the lens 6 will intercept both scattered and fluorescent light in two different polarization planes, the light which has passed through the quarter-wave plate 8 and is reflected back by the mirror reflector 9 being rotated by $\pi/2$ in relation to the laser beam's original polarization plane. This allows the detection to be performed in an optional polarization plane. As mentioned a photodiode in the form of an avalanche diode can be used in the detector 13, this being an advantage if the fluorescent light is weak in addition to making the use of a photomultiplier for light intensification superfluous. It should also be noted that in the design of the liquid flow cytometer according to the present invention, due to the double scattering in the metering zone a scatter signal of high intensity is achieved. Background noise is largely eliminated and a liquid cytometer is thus provided which is suitable for use in microbiology and which has the necessary stability, reliability and sensitivity.

Designed according to the present invention, the liquid flow cytometer has small dimensions and is simple to use. The analysis time is less than 10 s and the sample volume normally used is approximately 0.5 ml.

The liquid flow cytometer according to the present invention is suitable for analysis and counting of biological microparticles with diameters from 0.2–30µ in concentrations of between $10^3$ and $10^7$ particles pr. ml.

We claim:

1. A liquid flow cytometer for counting and classification of particles such as biological cells or other microscopic particles in liquids, where the cytometer comprises an optical system for irradiation and detection in a metering zone (7), thus enabling optical dispersion and fluorescence caused by the particles to be simultaneously detected when the particles pass the metering zone, wherein the optical system in a first beam path ($S_1$) comprises a mirror reflector (9) with its focal point in the metering zone (7), a quarter-wave plate (8) between the metering zone (7) and the mirror reflector (9), a lens (6) with its focal point in the metering zone (7) and located between the metering zone (7) and a dichroic mirror (5), the dichroic mirror (5) being provided in such a manner that it gives a partial reflection substantially orthogonal to the axis of the lens (6), the reflection direction being in a second beam path ($S_2$) of the optical system, and in the second beam path ($S_2$) a beam splitter (4) located between the dichroic mirror (5) and a light source (1), the beam splitter (4) producing a third beam path ($S_3$) orthogonal to the second beam path ($S_2$), wherein the cytometer further comprises a first detector (13) provided in the first beam path ($S_1$) after the dichroic mirror (5) and arranged for the detection of fluorescence emitted by the particles in the metering zone (7), together with a second detector (16) provided in the third beam path ($S_3$) and arranged for the detection of optical dispersion caused by the particles in the metering zone (7).

2. A cytometer according to claim 1 wherein, the mirror reflector (9) is a spherical concave mirror.

3. A cytometer according to claim 1 wherein, the beam splitter (4) is a polarizing beam splitter.

4. A cytometer according to claim 1, wherein a lens device (2,3) is provided in the second beam path ($S_2$) between the polarizing beam splitter (4) and the light source (1) for focusing of light from the light source (1) on to the beam splitter (4).

5. A cytometer according to claim 4, wherein the light source (1) is a diode laser provided in the second beam path ($S_2$).

6. A cytometer according to claim 5, wherein between the first detector (13) and the dichroic filter (5) an optical filter (10,11) together with a suitable lens device (12) are provided for focusing of fluorescent light which passes the dichroic mirror (5) and on the first detector (13).

7. A cytometer according to claim 6, wherein the first detector (13) comprises a photodiode.

8. A cytometer according to claim 1, wherein between the second detector (16) and the beam splitter (4) a beam stop (14) and a lens device (15) are provided for focusing of scattered light reflected by the beam splitter (4) onto the second detector (16).

9. A cytometer according to claim 7, wherein the second detector (16) comprises a photodiode.

10. A cytometer according to claim 6, wherein said photodiode is an avalanche diode.

11. A cytometer according to claim 9, wherein said photodiode is a PIN diode.

* * * * *